(12) United States Patent
Sowards et al.

(10) Patent No.: US 12,027,876 B2
(45) Date of Patent: Jul. 2, 2024

(54) WIRELESS MEDICAL DEVICE POWERING SYSTEM

(71) Applicant: Bard Access Systems, Inc., Salt Lake City, UT (US)

(72) Inventors: Steffan Sowards, Salt Lake City, UT (US); William Robert McLaughlin, Bountiful, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/677,704

(22) Filed: Feb. 22, 2022

(65) Prior Publication Data

US 2022/0271565 A1 Aug. 25, 2022

Related U.S. Application Data

(60) Provisional application No. 63/152,740, filed on Feb. 23, 2021.

(51) Int. Cl.
| | |
|---|---|
| *A61B 5/00* | (2006.01) |
| *A61B 5/0537* | (2021.01) |
| *A61B 5/0538* | (2021.01) |
| *H02J 50/12* | (2016.01) |
| *H03H 9/125* | (2006.01) |

(52) U.S. Cl.
CPC ............ *H02J 50/12* (2016.02); *H03H 9/125* (2013.01)

(58) Field of Classification Search
CPC ........ H02J 50/12; H02J 7/0068; H03H 9/125; A61B 5/0537; A61B 5/0538; A61B 2560/0219; A61B 5/6847
See application file for complete search history.

(56) References Cited

U.S. PATENT DOCUMENTS

| | | | | |
|---|---|---|---|---|
| 2015/0102681 A1* | 4/2015 | Leabman | ............ | H02J 7/00034 307/104 |
| 2021/0045864 A1* | 2/2021 | Pelssers | .............. | A61M 60/454 |
| 2021/0111762 A1* | 4/2021 | Lee | ........................ | H04B 5/0062 |
| 2021/0402164 A1* | 12/2021 | Mitchell | ................ | A61B 5/062 |

FOREIGN PATENT DOCUMENTS

| | | | | |
|---|---|---|---|---|
| EP | 3520706 A1 * | 8/2019 | ............... | A61B 8/12 |
| EP | 3520706 A1 | 8/2019 | | |
| WO | WO-2006041738 A2 * | 4/2006 | ........... | A61B 5/0031 |
| WO | 2020/106804 A1 | 5/2020 | | |

OTHER PUBLICATIONS

Whatls.com, " Definition of processor (CPU)," pp. 1-3, Aug. 2019 (Year: 2019).*
PCT/US2022/017327 filed Feb. 22, 2022 International Search Report and Written Opinion dated Jun. 10, 2022.

* cited by examiner

*Primary Examiner* — Elim Ortiz
(74) *Attorney, Agent, or Firm* — Rutan & Tucker LLP

(57) ABSTRACT

Disclosed herein is a wireless medical device powering system configured to power an untethered medical device including a first medical device having an induction receiving coil, the induction receiving coil in communication with each of one or more electrical systems and a first medical device console comprising one or more processors, a non-transitory computer readable medium, and a plurality of logic modules. The system can include a wireless powering device configured to wirelessly provide power to the first medical device, the wireless powering device having a body including an induction transmitting coil.

16 Claims, 7 Drawing Sheets

WIRELESS MEDICAL DEVICE POWERING SYSTEM

PRIORITY

This application claims the benefit of priority to U.S. Provisional Application No. 63/152,740, filed Feb. 23, 2021, which is incorporated by reference in its entirety into this application.

BACKGROUND

An increasing number of medical devices are incorporating electronic systems that may be configured to provide information including state of disease in a patient or location of the medical device in the patient to a clinician. These electronic systems must be powered by an energy source, including an external power source which can require the medical device to be tethered to the power source or a battery, which has a finite life span. Thus it would be beneficial to the clinician and the patient to be able to wirelessly provide energy to the medical device, allowing untethered medical devices to be used in procedures. Disclosed herein are a system and method that address the foregoing.

SUMMARY

Disclosed herein is a wireless medical device powering system configured to power an untethered medical device including a first medical device having an induction receiving coil, the induction receiving coil in communication with each of one or more electrical systems and a first medical device console comprising one or more processors, a non-transitory computer readable medium, and a plurality of logic modules. The system further including a wireless powering device configured to wirelessly provide power to the first medical device, the wireless powering device having a body including an induction transmitting coil.

In some embodiments, the induction receiving coil is configured to wirelessly receive power from the induction transmitting coil by inductive coupling.

In some embodiments, the first medical device includes a rechargeable energy source.

In some embodiments, the first medical device is selected from the group consisting of: a needle, an introducer, a catheter, a stylet, an obturator, a guidewire, a smart dressing, a port, a stent and a valve.

In some embodiments, the plurality of logic modules of the first medical device console is configured to perform one or more of tracking the status of the rechargeable energy source, activating the one or more electronic systems, transmitting data from the one or more electronic systems to the wireless powering device or a computing device, and transmitting the status of the rechargeable energy source to the wireless powering device or the computing device.

In some embodiments, the wireless powering device is coupled to a second medical device selected from the group consisting of: an ultrasound probe, a patch cable module, an EM sensor, an ECG module, a medical drill and a dedicated power source module.

In some embodiments, the one or more electronic systems is configured to acquire impedance measurements, perform tissue differentiation, perform vessel identification, perform vessel dimension and volume identification, perform ECG monitoring, perform timestamping, perform medical device identification, patency identification and monitoring.

In some embodiments, the wireless powering device includes a wireless powering device console having one or more processors and a non-transitory computer readable medium having a plurality of logic modules.

In some embodiments, the plurality of logic modules of the wireless powering device console is configured to perform one or more of activating the wireless powering device, transmitting the wireless power from the induction transmitting coil to the induction receiving coil, determining the amount of power to wirelessly distribute to the first medical device, indicating the status of the wireless power transmission, and transmitting the status of the wireless power transmission to a computing device.

Also disclosed herein is a method of wirelessly providing power to a first medical device including configuring a wireless medical device powering system for power distribution, placing a wireless powering device of the wireless medical device powering system in proximity to the first medical device, and distributing power to the first medical device.

In some embodiments, the wireless medical device powering system includes the wireless powering device and the first medical device.

In some embodiments, the first medical device includes an induction receiving coil, one or more electronic systems, and a first medical device console having one or more processors, non-transitory computer readable medium and a plurality of logic modules.

In some embodiments, the wireless powering device includes an induction transmitting coil coupled to an energy source.

In some embodiments, the first medical device includes a rechargeable energy source.

In some embodiments, the wireless powering device is coupled to a second medical device.

In some embodiments, configuring includes coupling the wireless powering device to the second medical device.

In some embodiments, distributing power to the first medical device includes distributing power from the induction transmitting coil to the induction receiving coil by induction, inductive coupling or resonant inductive coupling.

In some embodiments, distributing power includes moving the wireless powering device over the first medical device.

In some embodiments, the first medical device includes a needle, an introducer, a catheter, a stylet, an obturator, a guidewire, a smart dressing, a port, a stent or a valve.

In some embodiments, the second medical device includes an ultrasound probe, a patch cable module, a magnet sensor, an EM sensor, an ECG module, or a medical drill.

In some embodiments, the first medical device includes one or more electrical systems configured to perform functions selected from the group consisting of impedance measurements, tissue differentiation, vessel identification, vessel dimension and volume identification, ECG monitoring, timestamping, medical device identification, patency identification, monitoring, and combinations thereof.

Also disclosed herein is a wireless medical device powering system, configured to power an untethered medical device, including a needle having an induction receiving coil, an impedance measuring device and an impedance measuring device console, the induction receiving coil in communication with each of the impedance measuring device, and the impedance measuring device console comprising one or more processors, a non-transitory computer readable medium, and a plurality of logic modules, and a wireless powering device configured to wirelessly provide power to the induction receiving coil, the wireless powering device having a body including an induction transmitting coil, and being coupled to an ultrasound probe.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
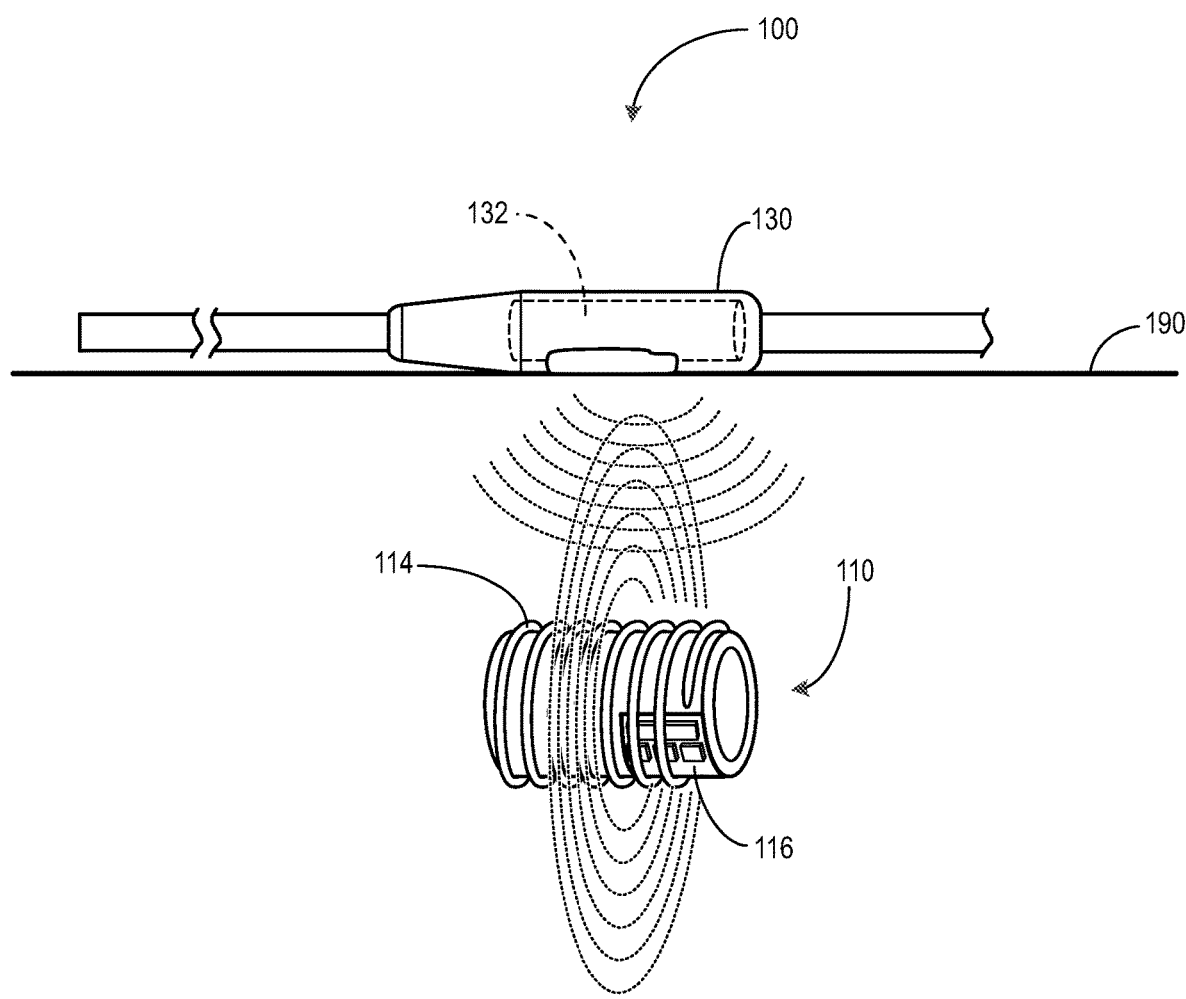
FIG. 1 illustrates a perspective view of a wireless medical device powering system, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a medical device disclosed herein includes a portion of the first medical device intended to be near a clinician when the first medical is used on a patient. Likewise, a "proximal length" of, for example, the first medical device includes a length of the first medical device intended to be near the clinician when the first medical device is used on the patient. A "proximal end" of, for example, the first medical device includes an end of the first medical device intended to be near the clinician when the first medical device is used on the patient. The proximal portion, the proximal-end portion, or the proximal length of the first medical device can include the proximal end of the first medical device; however, the proximal portion, the proximal-end portion, or the proximal length of the first medical device need not include the proximal end of the first medical device. That is, unless context suggests otherwise, the proximal portion, the proximal-end portion, or the proximal length of the first medical device is not a terminal portion or terminal length of the first medical device.

With respect to "distal," a "distal portion" or a "distal-end portion" of, for example, a medical device disclosed herein includes a portion of the first medical device intended to be near or in a patient when the first medical device is used on the patient. Likewise, a "distal length" of, for example, the first medical device includes a length of the first medical device intended to be near or in the patient when the first medical device is used on the patient. A "distal end" of, for example, the first medical device includes an end of the first medical device intended to be near or in the patient when the first medical device is used on the patient. The distal portion, the distal-end portion, or the distal length of the first medical device can include the distal end of the first medical device; however, the distal portion, the distal-end portion, or the distal length of the first medical device need not include the distal end of the first medical device. That is, unless context suggests otherwise, the distal portion, the distal-end portion, or the distal length of the first medical device is not a terminal portion or terminal length of the first medical device.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Unless defined otherwise, all technical and scientific terms used herein have the same meaning as commonly understood by those of ordinary skill in the art.

FIG. 1 illustrates a perspective view of a wireless medical device powering system, in accordance with some embodiments. In some embodiments, the wireless medical device powering system ("system") 100 includes a first untethered medical device ("medical device") 110 and a wireless powering device 130. As used herein, untethered includes a medical device that is physically unconnected from the wireless powering device 130. In some embodiments, the wireless powering device 130 may be configured to wirelessly transmit power to the first medical device 110. In some embodiments, the wireless powering device 130 may be configured to subsequently or simultaneously wirelessly transmit power to two or more medical devices. In some embodiments, the first medical device 110 includes an induction receiving coil 114 in communication with one or more electronic systems 116 thereon. In some embodiments, the first medical device 110 may include an implanted medical device (e.g., a catheter, a guidewire, a stent, a valve, a port), a medical device that sits on a skin surface (e.g., a dressing, a bandage), or a temporary implanted medical device (e.g., a needle, an introducer, a stylet, an obturator), or the like. In some embodiments, the induction receiving coil 114 and the one or more electronic systems 116 may be coupled to the first medical device 110 or contained within the first medical device 110. In some embodiments, the one or more electrical systems 116 may include an impedance measuring system, a tissue differentiation system, an ECG monitoring system, a blood vessel dimension detecting system, a blood vessel volume identification system, a medical device identification system, a blood vessel identification system or the like.

In some embodiments, the system 100 includes a wireless powering device 130, configured to wirelessly provide power to the first medical device 110, that will be described in more detail herein. In some embodiments, the wireless powering device 130 may include an induction transmitting coil 134. In some embodiments, the wireless powering device 130 may be coupled to a second medical device. The second medical device may be configured to stay on or above a skin surface 190 of a patient. The first medical device 110 is untethered to the wireless powering device 130 but is in wireless communication with the wireless powering device 130. The wireless powering device 130 may be configured to provide power to the first medical device 110 through induction or inductive coupling of the induction transmitting coil 134 to the induction receiving coil 114. Advantageously, providing power to the first medical device 110 through induction or inductive coupling allows the first medical device 110 to include one or more electronic systems 116 thereon, quickly providing clinicians access to relevant medical data. In a preferred embodiment, the first medical device 110 includes a needle wherein the one or more electronic systems 116 include an impedance measuring device and the wireless powering device 130 is coupled to a second medical device, wherein the second medical device includes an ultrasound probe. In this embodiment, the wireless powering device 130 coupled to the ultrasound probe wirelessly transmits power to the induction receiving coil 114 configured to power the impedance measuring device 116 on the needle.

FIGS. 2A-2D illustrate perspective views of various embodiments of the first medical device 110, in accordance with some embodiments. In some embodiments, the first medical device 110 may include a medical device body 112, having the induction receiving coil 114 and the one or more electronic systems 116 thereon. In some embodiments, the first medical device 110 may be located on or below the skin surface 190 of the patient.

Figure 2A:
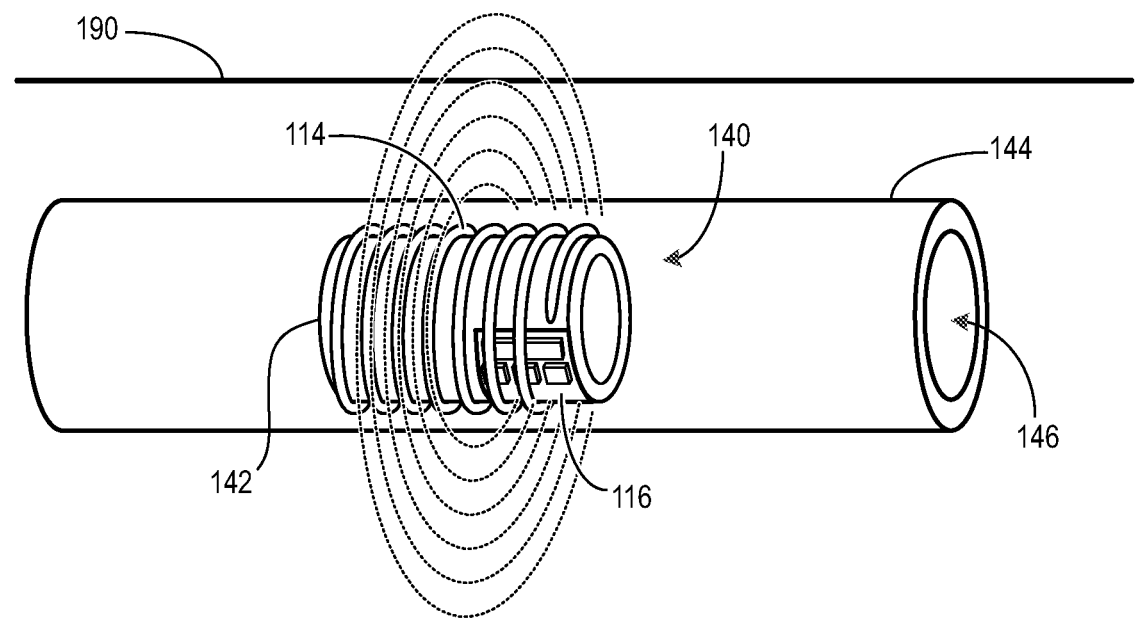
FIGS. 2A-2D illustrate perspective views of various embodiments of the first medical device including an induction receiving coil, in accordance with some embodiments.
Figure 2B:
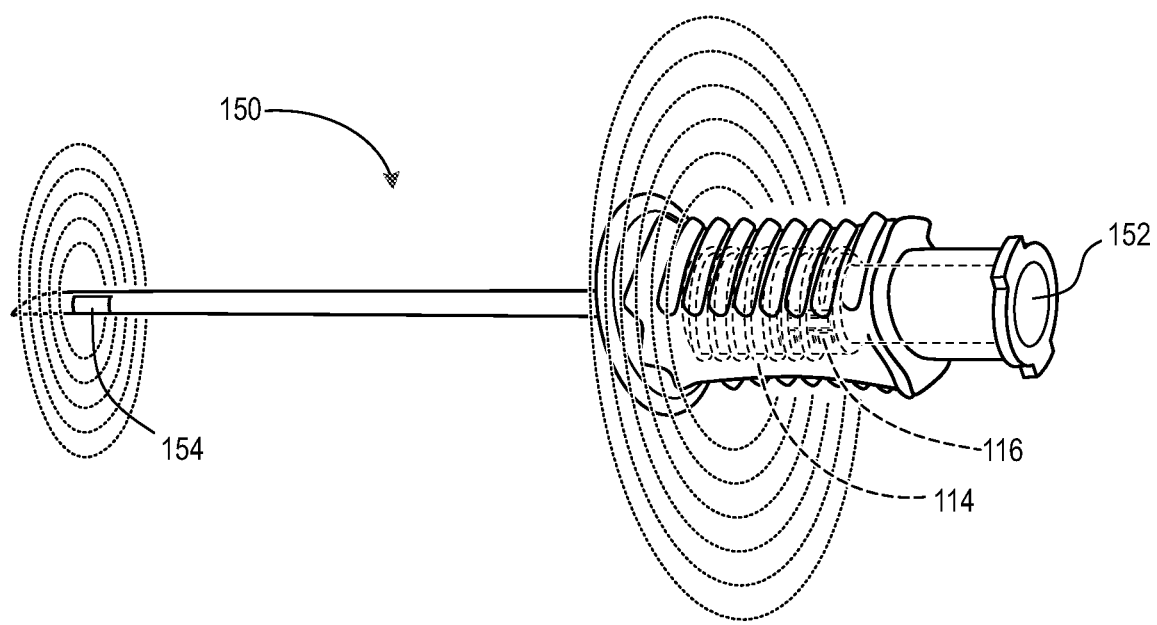

In an embodiment, as illustrated in FIG. 2A, the first medical device 110 may include a stent 140, having a stent body 142 including the induction receiving coil 114 and an electrical system 116 thereon. The stent 140 may be configured to be inserted into a lumen 146 of a blood vessel 144. The induction receiving coil 114 may receive and provide power to the electrical system 116 which may be configured to detect and measure the diameter of the blood vessel 144, dimensions of the blood vessel 144 and measure blood flow. In an embodiment, as illustrated in FIG. 2B, the first medical device 110 may include a needle 150 having a needle hub 152 and having the induction receiving coil 114 thereon. The needle hub 152 may include the electrical system 116 with one or more sensors 154 coupled to the needle 150. In some embodiments, the one or more sensors 154 may be configured to differentiate tissues or vessels during insertion. In some embodiments, the induction receiving coil 114 may be coupled to the needle hub 152 or incorporated into the needle hub 152. For example, the induction receiving coil 114 and electrical system 116 may be embedded in the needle hub 152 as shown in FIG. 2B and FIG. 2E.

Figure 2C:
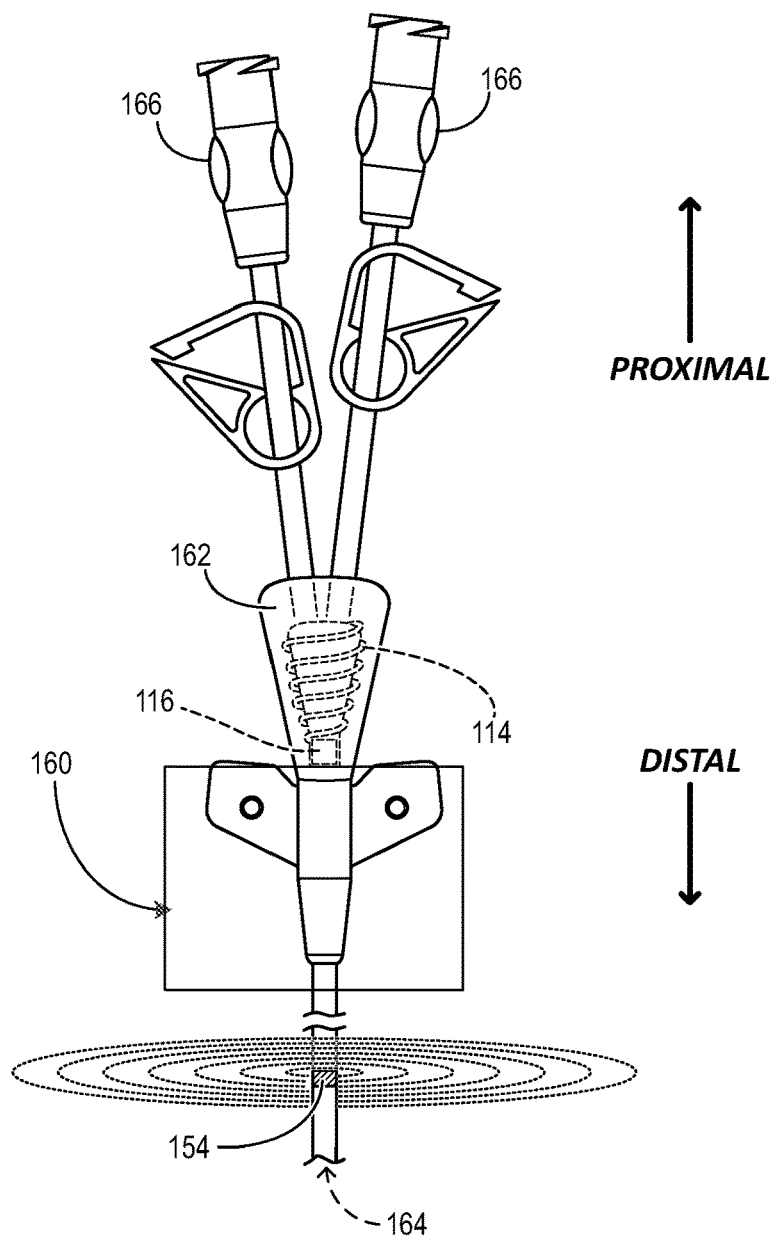
Figure 2D:
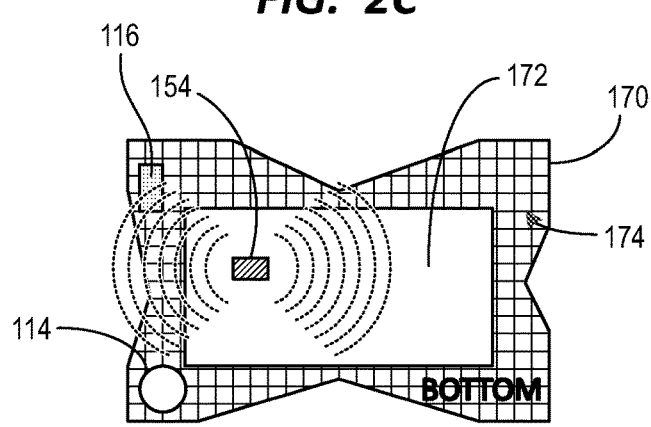

In an embodiment, as illustrated in FIG. 2C, the first medical device 110 may include a catheter 160. As used herein a "catheter" can include a catheter, peripherally inserted central catheter ("PICC"), peripheral intravenous line ("Ply"), central venous catheter ("CVC"), midline catheter, or the like etc. In some embodiments, the catheter 160 may include a hub 162, a catheter lumen 164 and one or more extension legs 166. The catheter 160 may include the induction receiving coil 114 and the one or more electronic systems 116 thereon. In some embodiments, the induction receiving coil 114 may be located at a proximal end of the catheter 150. In some embodiments, as illustrated in FIG. 2C, the induction receiving coil 114 may be coupled to the hub 162, e.g., embedded in the hub 162. In some embodiments, the electronic system 116 may be coupled to the hub 162. In some embodiments, the electronic system 116 may include the one or more sensors 154 located proximally, distally or a combination thereof. The electronic system 116 and one or more sensors 154 may be configured to detect impedance measurements, identify and monitor patency within the catheter 160 or perform ECG monitoring. In an embodiment, as illustrated in FIG. 2D, the first medical device 110 may include a bandage 170. In this embodiment, the bandage 170 may include a top side and a bottom side, wherein the bottom side includes an adhesive compound 174 thereon and an absorbent pad 172. In this embodiment, the bandage 170 includes the induction receiving coil 114 on the top or bottom side. In this embodiment, the bandage 170 includes the one or more electronic systems 116 including the one or more sensors 154. In this embodiment, the sensor 154 may be coupled to the absorbent pad 172. The electronic system 116 and the sensor 154 may be configured to measure and detect various outcomes on the bandage 170.

Figure 2E:
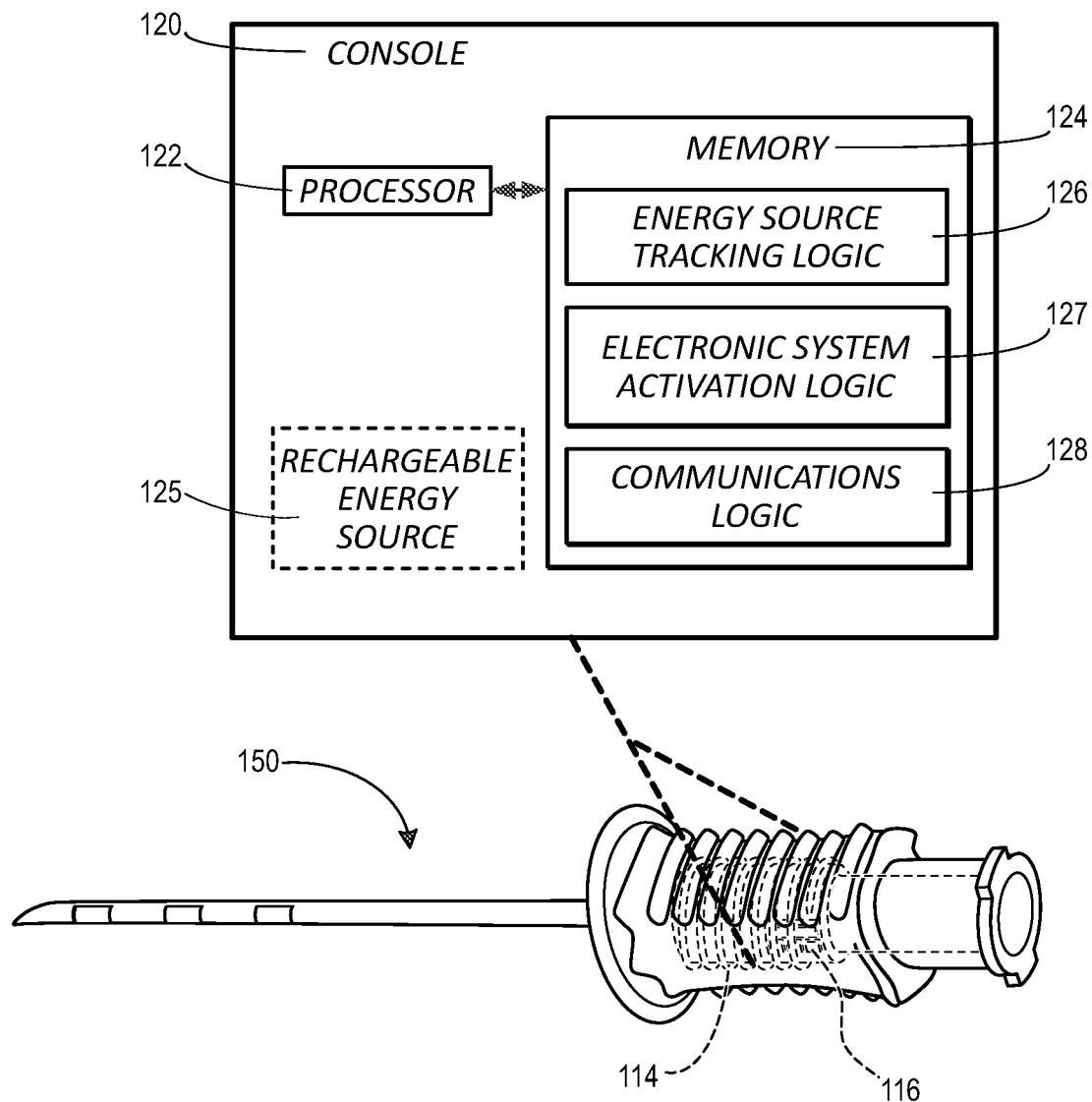
FIG. 2E illustrates some components of the first medical device including the first medical device console, in accordance with some embodiments.

FIG. 2E illustrates some components of the first medical device 110 including a medical device console 120, in accordance with some embodiments. In some embodiments, the first medical device 110 may be configured to include the first medical device console 120. In some embodiments, the first medical device console 120 may be coupled to the one or more electronic systems 116. In some embodiments, the first medical device console 120 may be coupled to an outside of the first medical device 110 or incorporated within the first medical device 110. In some embodiments, the first medical device console 120 may include one or more processors 122, non-transitory computer readable medium ("memory") 124 including a plurality of logic modules. In some embodiments, the first medical device console 120 includes a rechargeable energy source 125 coupled to the induction receiving coil 114 and the one or more electronic systems 116.

In some embodiments, the induction receiving coil 114 may be configured to recharge the rechargeable energy source 125 from the wireless power received by the wireless powering device 130. In some embodiments, the plurality of logic modules may include one or more of: an energy source tracking logic 126, an electronic system activation logic 127 and a medical device communications logic 128. In some embodiments, the energy source tracking logic 126 may be configured to track the status of the rechargeable energy source 125. In some embodiments, the status may include the capacity (e.g., 50% capacity, 10% capacity, 5% capacity) of the rechargeable energy source 125. In some embodiments, the electronic system activation logic 127 may be configured to activate the one or more electronic systems 116 for their various functions as described above. In some embodiments, the first medical device communications logic 128 may be configured to transmit any acquired data from the one or more electronic systems 116 to the wireless powering device 130 or the computing device. In some embodiments, the first medical device communications logic 128 may be configured to transmit the status of the rechargeable energy source 125 to the wireless powering device 130 or a computing device. In the preferred embodiment, the needle may be configured to include an impedance measuring device console as described above.

Figure 3:
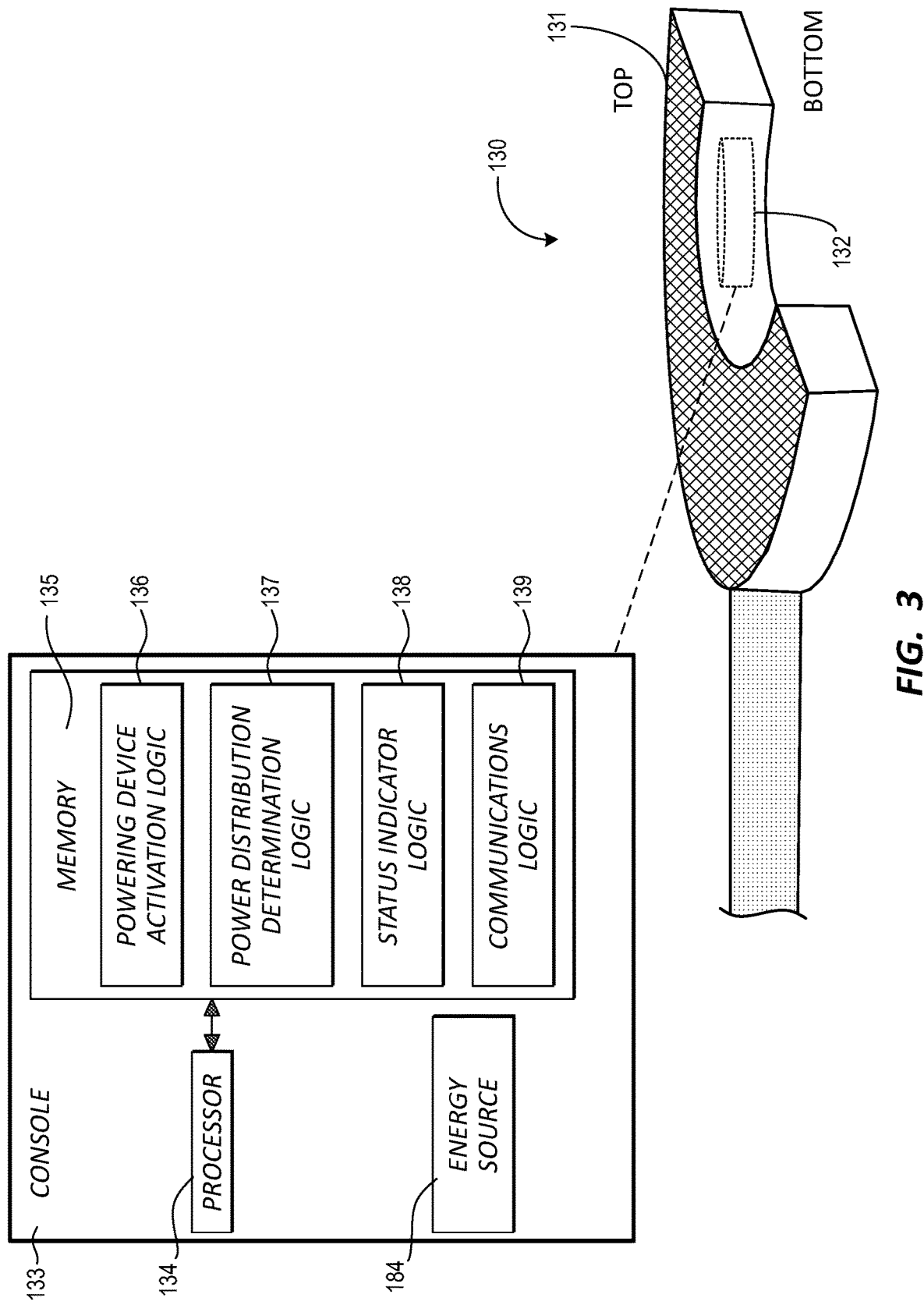
FIG. 3 illustrates some components of the wireless powering device including the wireless powering device console, in accordance with some embodiments.

FIG. 3 illustrates a perspective view of some components of the wireless powering device 130 in accordance with some embodiments. In some embodiments, the wireless powering device 130 may include a wireless powering device body 131. In some embodiments, the wireless powering device body 131 may have a top side and a bottom side. The wireless powering device body 131 including an induction transmitting coil 132 configured to wirelessly transmit power to the induction receiving coil 114. The wireless powering device 130 includes a wireless powering device console 133 thereon or therein. In some embodiments, the wireless powering device console 133 may include one or more processors 134, an energy source 184, non-transitory computer readable medium ("memory") 135 and a plurality of logic modules. In some embodiments, the plurality of logic modules may include one or more of: a powering device activation logic 136, a power distribution determination logic 137, a status indicator logic 138, a communications logic 139. In some embodiments, the powering device activation logic 136 may be configured to activate the wireless powering device 130 and transmit the wireless power from the induction transmitting coil 132.

Figure 4B:
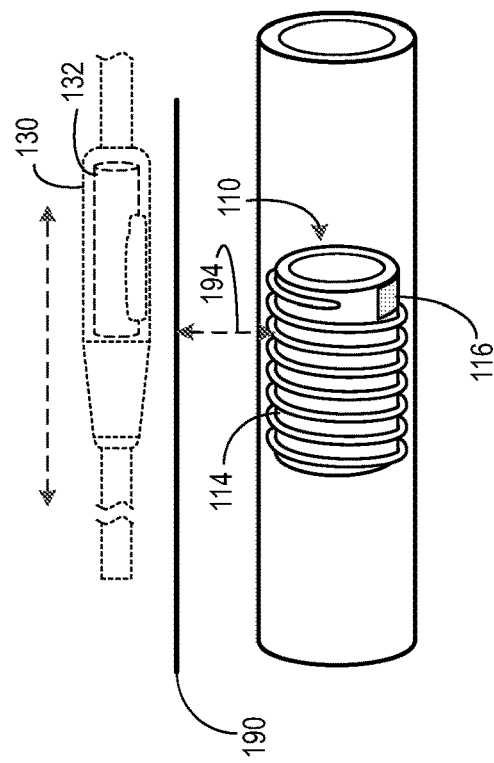
FIGS. 4A-4B illustrate an exemplary method of wirelessly providing power to the first medical device, in accordance with some embodiments.
Figure 4A:
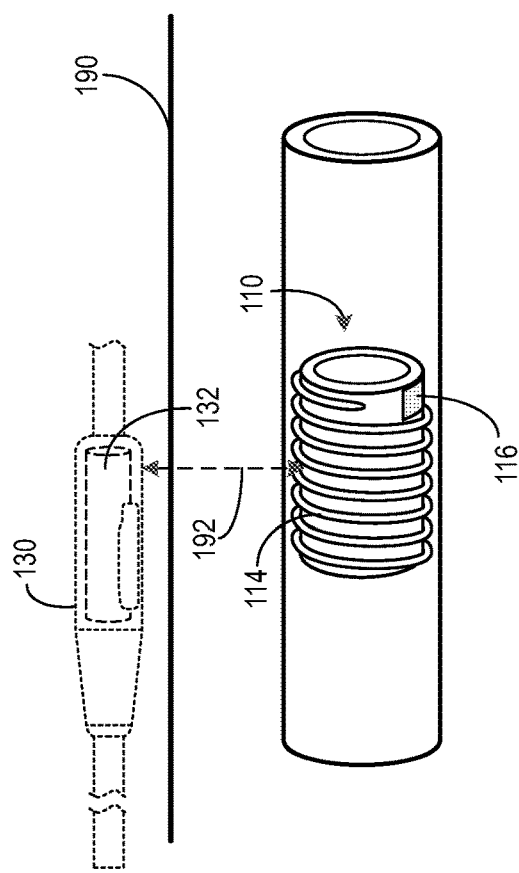

In some embodiments, the wireless power distribution determination logic 137 may be configured to determine the amount of power needed for transmission. In some embodiments, the wireless power distribution determination logic 137 may be configured to transmit a predetermined or a user defined amount of power to the first medical device 110. In some embodiments, the status indicator logic 138 may be configured to indicate the status of wireless power transmission from the induction transmitting coil 132. In some embodiments, the communications logic 139 may be configured to transmit the status of the wireless power transmission from the induction transmitting coil 132 to a computing device. In some embodiments, the wireless powering device 130 may include a dedicated power source module (e.g., wand, remote, power pad) coupled to the induction transmitting coil 134. In some embodiments, the wireless powering device 130 may be configured to includes one or more magnets coupled to the induction transmitting coil 132. In some embodiments, the wireless powering device 130 may be coupled to a second medical device. In some embodiments, the second medical device includes an ultrasound probe, a patch cable module, a magnet sensor, an EM sensor, an ECG module, a medical drill or the like. In some embodiments, movement of the second medical device may be configured to generate the power transmitted from the induction transmitting coil 132. The wireless powering device 130 may be in communication with a computing device or a display. The wireless powering device 130 may include a status indicator (e.g., an LED, a status bar icon or the like) configured to indicate to a user the status or time remaining left of the wireless power transmission FIGS. 4A-4B illustrate an exemplary method of wirelessly providing power to a medical device 110 using a wireless medical device powering system 100, in accordance with some embodiments. In some embodiments, as illustrated in FIG. 4A, the first medical device 110 may be implanted into a body of a patient or placed on a skin surface 190 of a patient. In some embodiments, the first medical device 110 and the wireless powering device 130 may be physically separate by a first distance 192. In some embodiments, the first distance 192 may include one or more tissues including the skin surface 190. As illustrated in FIG. 4B, the wireless powering device 130 may be brought in proximity of the first medical device 110. Proximity may include a second distance 194 that is smaller than the first distance 192. The wireless powering device 130 may remain in the proximity of the first medical device 110 or may be removed from proximity to the first medical device 110. In some embodiments, the wireless powering device 130 may be moved along the skin surface 190, in proximity to the first medical device 110.

Figure 5:
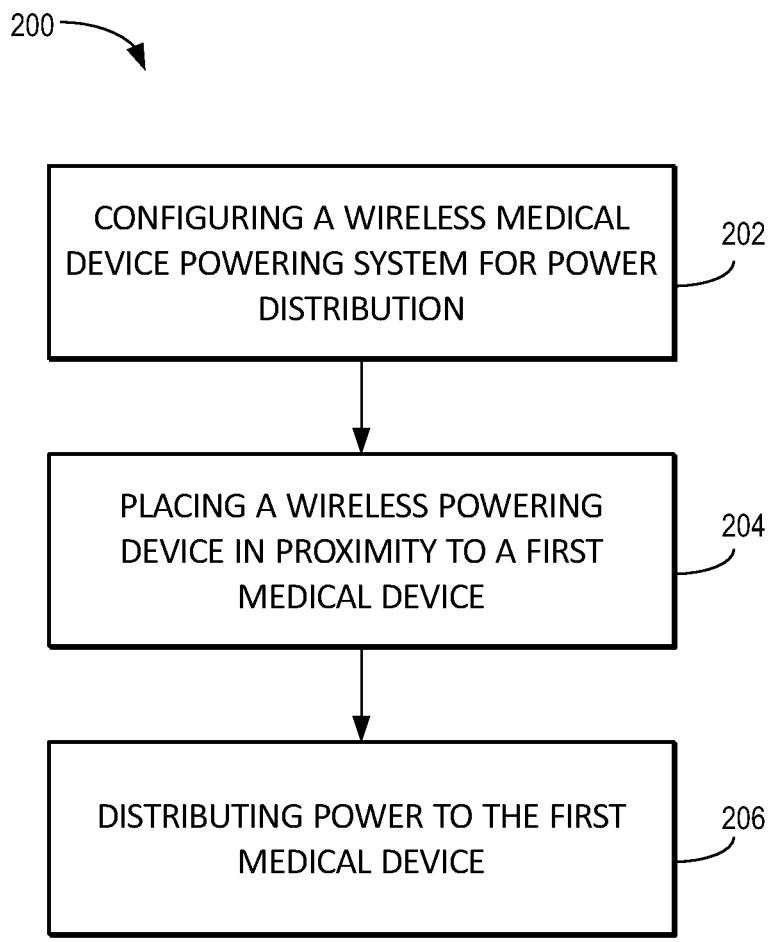
FIG. 5 illustrates a flow chart of an exemplary method of wireless providing power to the first medical device, in accordance with some embodiments.

FIG. 5 illustrates a flow chart of the exemplary method 200 of wirelessly providing power to the first medical device 110, in accordance with some embodiments. The method 202 including configuring a wireless medical device powering system 100 including a wireless powering device 130 for power distribution to a first medical device 110 (block 202). In some embodiments, the first medical device 110 and the wireless powering device 130 may be separated by a first distance 192. In some embodiments, configuring includes coupling the wireless powering device 130 to a second medical device. In some embodiments, configuring includes activating the wireless powering device 130. In some embodiments, the wireless powering device 130 may include the induction transmitting coil 132. In some embodiments, the first medical device 110 includes the induction receiving coil 114 and the one or more electronic systems 116 thereon.

The method 200 includes placing the wireless powering device 130 in proximity to the first medical device 110 (block 204). In some embodiments, in proximity includes the wireless powering device 130 in communication with the first medical device 110. In some embodiments, in proximity includes the wireless powering device 130 and the first medical device 110 separated by a second distance 194. The method 200 includes distributing power to the first medical device 110 (block 206). In some embodiments, distributing power includes distributing power through induction, inductive coupling or resonant inductive coupling. In some embodiments, distributing power includes distributing power from the induction transmitting coil 134 of the wireless powering device 130 to the induction receiving coil 114 of the first medical device 110. In some embodiments, distributing power includes distributing power until the rechargeable energy source 125 is completely recharged. In some embodiments, distributing power including distributing power to the first medical device 110 while the one or more electronic systems 116 are in use.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A wireless medical device powering system configured to power an untethered medical device, comprising:
    a needle having an induction receiving coil, the induction receiving coil in communication with each of:
        one or more electronic systems; and
        a needle console comprising one or more processors, a non-transitory computer readable medium, and a plurality of logic modules thereon; and
    a wireless powering device coupled to an ultrasound probe, the wireless powering device configured to wirelessly provide power to the needle, the wireless powering device having a body including an induction transmitting coil.

2. The wireless medical device powering system according to claim 1, wherein the induction receiving coil is configured to wirelessly receive power from the induction transmitting coil by inductive coupling.

3. The wireless medical device powering system according to claim 1, wherein the needle includes a rechargeable energy source.

4. The wireless medical device powering system according to claim 1, wherein the plurality of logic modules of the needle console is configured to perform one or more of:
    tracking a status of a rechargeable energy source of the needle;
    activating the one or more electronic systems;
    transmitting data from the one or more electronic systems to the wireless powering device or a computing device; and
    transmitting the status of the rechargeable energy source to the wireless powering device or the computing device.

5. The wireless medical device powering system according to claim 1, wherein the one or more electronic systems are configured to acquire impedance measurements, perform tissue differentiation, perform vessel identification, perform vessel dimension and volume identification, perform ECG monitoring, perform timestamping, perform medical device identification, patency identification and monitoring, or a combination thereof.

6. The wireless medical device powering system according to claim 1, wherein the wireless powering device includes a wireless powering device console having one or more processors and a non-transitory computer readable medium having a plurality of logic modules.

7. The wireless medical device powering system according to claim 6, wherein the plurality of logic modules of the wireless powering device console is configured to perform one or more of:
    activating the wireless powering device;
    wirelessly transmitting power from the induction transmitting coil to the induction receiving coil;
    determining an amount of power to wirelessly distribute to the needle;
    indicating a status of wireless power transmission; and
    transmitting the status of the wireless power transmission to a computing device.

8. A method of wirelessly providing power to a needle, comprising:
    placing a wireless powering device of a wireless medical device powering system in proximity to the needle, the wireless powering device coupled to an ultrasound probe; and
    distributing power to the needle.

9. The method according to claim 8, wherein the wireless medical device powering system includes the wireless powering device and the needle.

10. The method according to claim 9, wherein the needle includes an induction receiving coil, one or more electronic systems, and a needle console having one or more processors, non-transitory computer readable medium and a plurality of logic modules.

11. The method according to claim 10, wherein the wireless powering device includes an induction transmitting coil coupled to an energy source.

12. The method according to claim 11, wherein distributing power to the needle includes distributing power from the induction transmitting coil to the induction receiving coil by induction, inductive coupling, or resonant inductive coupling.

13. The method according to claim 8, wherein the needle includes a rechargeable energy source.

14. The method according to claim 8, wherein distributing power to the needle includes moving the wireless powering device over the needle.

15. The method according to claim 8, wherein the needle includes one or more electronic systems configured to perform functions selected from the group consisting of impedance measurements, tissue differentiation, vessel identification, vessel dimension and volume identification, ECG monitoring, timestamping, medical device identification, patency identification and monitoring, and combinations thereof.

16. A wireless medical device powering system, configured to power an untethered medical device, comprising:
- a needle having an induction receiving coil;
- an impedance measuring device in communication with the induction receiving coil;
- an impedance measuring device console in communication with the induction receiving coil, the impedance measuring device console comprising one or more processors, a non-transitory computer readable medium, and a plurality of logic modules; and
- a wireless powering device coupled to an ultrasound probe, the wireless powering device including a body having an induction transmitting coil, the wireless powering device configured to wirelessly provide power to the induction receiving coil.

* * * * *